(12) United States Patent
Timmis et al.

(10) Patent No.: US 8,776,620 B2
(45) Date of Patent: Jul. 15, 2014

(54) FLUID SAMPLING DEVICE

(75) Inventors: Roger J. Timmis, Camforth (GB); Kevin C. Jones, Lancaster (GB)

(73) Assignee: Lancaster University Business Enterprises Limited, Lancaster (GB)

( * ) Notice: Subject to any disclaimer, the term of this patent is extended or adjusted under 35 U.S.C. 154(b) by 341 days.

(21) Appl. No.: 12/733,606

(22) PCT Filed: Sep. 11, 2008

(86) PCT No.: PCT/GB2008/050815
§ 371 (c)(1),
(2), (4) Date: Mar. 9, 2010

(87) PCT Pub. No.: WO2009/034389
PCT Pub. Date: Mar. 19, 2009

(65) Prior Publication Data
US 2010/0199785 A1    Aug. 12, 2010

(30) Foreign Application Priority Data
Sep. 13, 2007   (GB) .................................. 0717845.2

(51) Int. Cl.
*G01N 1/22* (2006.01)
(52) U.S. Cl.
USPC .................. 73/863.22; 73/863.31; 73/864.71; 73/863.51

(58) Field of Classification Search
CPC ...... G01N 1/2208; G01N 1/2273; G01N 1/26
USPC .............. 73/863.31, 863.51, 863.71, 863.22, 73/864.71
See application file for complete search history.

(56) References Cited

U.S. PATENT DOCUMENTS

| | | | | |
|---|---|---|---|---|
| 2,699,679 A | * | 1/1955 | Munger ...................... | 73/863.21 |
| 3,511,099 A | * | 5/1970 | Harsha ........................ | 73/863.11 |
| 3,780,566 A | * | 12/1973 | Smith et al. ................. | 73/31.01 |
| 4,437,333 A | * | 3/1984 | Hands .......................... | 73/12.11 |
| 5,040,424 A | * | 8/1991 | Marple et al. .............. | 73/863.23 |
| 5,739,439 A | * | 4/1998 | Gruidel et al. ................. | 73/864 |
| 2003/0033890 A1 | * | 2/2003 | Rodgers ..................... | 73/863.43 |
| 2005/0279181 A1 | * | 12/2005 | Trakumas et al. ......... | 73/863.22 |

FOREIGN PATENT DOCUMENTS

| | | |
|---|---|---|
| DE | 1091366 | 10/1960 |
| EP | 0571945 | 12/1993 |
| FR | 2677124 | 12/1992 |
| WO | WO 0210712 | 2/2002 |
| WO | WO 2008032116 | 3/2008 |

OTHER PUBLICATIONS

International Search Report for PCT appl. No. PCT/GB2008/050815, filed Sep. 11, 2008.

* cited by examiner

*Primary Examiner* — Hezron E Williams
*Assistant Examiner* — Nashmiya Fayyaz
(74) *Attorney, Agent, or Firm* — Alix, Yale & Ristas, LLP

(57) ABSTRACT

Disclosed is a fluid sampling device comprising a plurality of inlet channels, each of which is arranged to receive an airflow from an associated direction, such that a sampling medium associated with a particular inlet channel is exposed to airflow from the associated direction.

18 Claims, 5 Drawing Sheets

FLUID SAMPLING DEVICE

The present invention relates to fluid sampling devices and more particularly, but not exclusively, to fluid sampling devices able to provide directional information and requiring no power source.

It is desirable when performing environmental monitoring studies to sample airflow, and later to analyse the sampled flow for the presence of one or more substances, including without limitation pollutants.

Typical locations where pollutants may be monitored include: in the vicinity of fossil fuel burning power stations; chemical factories; landfills; or major roads.

There is no limit on the range of different pollutants which can cause environmental problems. In problem situations, or even just as a routine measure, it is normal to sample air-borne pollutants to ensure that safe levels are not exceeded, and to gather evidence for possible enforcement action.

Air-borne pollutants can include gaseous compounds or airborne particulate material (aerosols).

Current devices tend to be either very simple, such as diffusion tubes which have no directional resolution and may be simply affixed to a suitable surface in the vicinity of where samples are needed, or very complex, such as sampling devices housed in temporary buildings, requiring power sources and vandal-protection equipment. Moreover, these complex devices require site visits by specialist field personnel for purposes of instrument calibration and maintenance.

A problem with the simpler device is that the data it is able to yield only provide an indication that a particular pollutant was present in the vicinity of the sampler at some time during its deployment and does not identify the direction from which it came. However, such devices have the advantage that they are very cheap and easy to deploy and can therefore be used in large numbers in order to provide data from a wide area.

A problem with the more complex device is that it is comparatively expensive, bulky, and requires a suitable vacant site which may have implications for planning permission etc. Moreover, any vacant site that is available may not be where monitoring is most required. e.g. down (prevailing) wind of an industrial installation. It may also be intrusive and prone to tampering and/or vandalism. If it is necessary to sample from several locations, it may not be possible to site enough of the devices to ensure adequate coverage. However, such a device is able to offer more comprehensive data, including the time that particular samples are taken, together with the direction from which the prevailing wind was blowing at that time.

In situations where it is desirable to provide several sampling devices in such a way that directional data may be analysed with a view to locating the source of a particular pollutant, it is not generally possible to do this with current sampling devices. The use of several simple non-directional devices does not provide the required directional sensitivity and the use of several of the more complex devices is not generally practicable, due to cost considerations and to the difficulty of finding enough secure and power-supplied sites for locating such complex devices.

Embodiments of the present invention aim to address these and other problems with the prior art, whether mentioned herein or not.

According to a first aspect of the present invention, there is provided a fluid sampling device comprising a plurality of inlet channels, each of which is arranged to receive an airflow from an associated direction, such that a sampling medium associated with a particular inlet channel is exposed to airflow from the associated direction.

Preferably, the device comprises no moving parts.

Preferably the device comprises as many inlet channels as are required for a given angular resolution. i.e. 12 inlet channels will give a resolution of 30°; 20 inlet channels will give a resolution of 18° and so on.

Preferably the device is shaped such that it guides and receives air into whichever inlet channel is facing upwind at any given time, but also such that air is hindered from entering other inlet channels that are not then facing upwind. Moreover, the device is shaped such that airflows through each inlet channel occur in one direction only, and that 'backflows' in the opposite direction are minimized or prevented.

Preferably the device contains within each inlet channel a medium and/or cavity for sampling of airborne pollutants that arrive from the direction which the channel faces. The medium and/or cavity collect samples from the flux of pollutants that flows through the channel when the wind is aligned with its entrance. By contrast, the same medium and/or cavity is relatively sheltered from airflows and pollutant fluxes when the wind is from any other direction, although another channel will then face the wind and receive more airflows and pollutant fluxes for sampling. In this way different inlet channels are ventilated to a greater or lesser extent by winds from different directions, such that the device can differentiate between sampled air pollutants coming from different directions.

Preferably the inlet channel is arranged to provide a degree of differentiation for samples associated with relatively higher or lower wind speeds.

Preferably the degree of differentiation is provided by a bend in the inlet channel which causes differential changes in fluid flow through the channel.

Particular embodiments of the invention are described below that use alternative media, cavities, shapes and collection surfaces for passive directional sampling of air pollutants. These embodiments allow the invention to be adapted for use with different types of pollutants as may be found near different pollutant sources and emitting activities.

Other preferred features of the invention will be apparent from the description and Figures which follow.

For a better understanding of the invention, and to show how embodiments of the same may be carried into effect, reference will now be made, by way of example, to the accompanying diagrammatic drawings in which.

Figure 1:
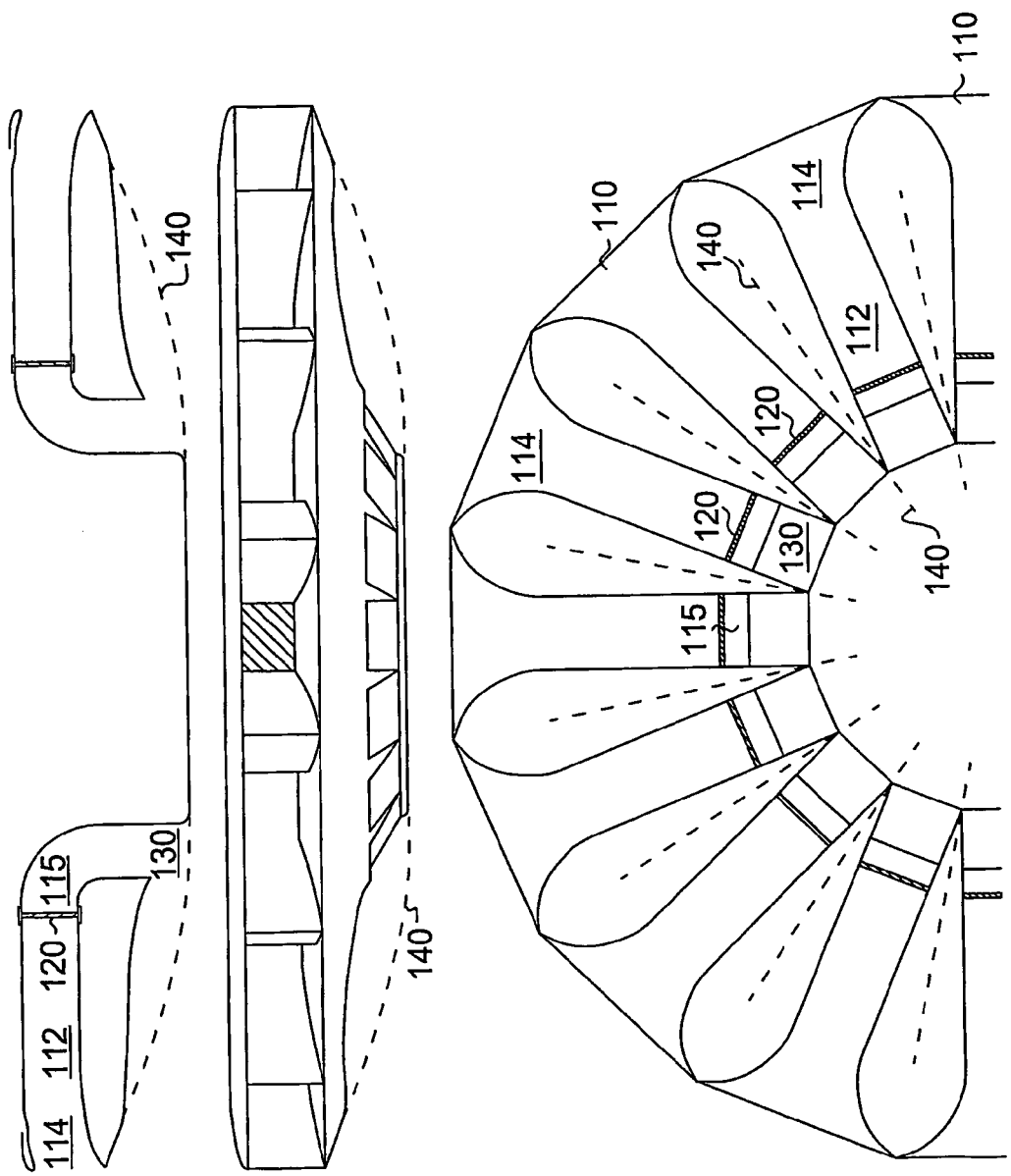
FIG. 1A shows a central cross sectional view through a first embodiment of the present invention.
FIG. 1B shows a front elevation of the first embodiment of the present invention.
FIG. 1C shows a cross sectional plan view of the first embodiment of the present invention.

FIGS. 1A to 1C show various views of a first embodiment of the present invention. FIG. 1O shows only half the plan view of the device as it is entirely symmetrical and no detail is thus omitted. These figures show a directional passive air sampler 100 which is arranged to resolve the direction of arrival of sampled airborne pollutants. The sampler comprises a plurality of inlet channels 110 arranged around the circumference of the sampler, each one occupying, in this case, 22.5° of the overall perimeter. There are therefore sixteen inlet channels 110 in this particular embodiment. Other embodiments may employ a greater or smaller number of inlet channels 110 to provide a different degree of angular resolution.

Each inlet channel 110 comprises a length of parallel-sided duct 112 with rectangular cross-section at an inner portion of the channel 110. The outer section comprises a flared horn structure 114 which leads into the parallel-sided duct 112. The upper surface of the flared horn 114 is angled slightly downward from the horizontal to help prevent the ingress of rain or other precipitation into the parallel-sided duct 112. The lower surface of the flared horn 114 is also angled downward from the horizontal to help prevent ingress of rain or other precipitation into the parallel-sided duct 112, and to help guide airflows and airborne pollutants arriving from the relevant direction into the parallel-sided duct 112.

As can be seen most clearly in FIG. 1A, air entering the inlet horn 114 passes down the parallel-sided rectangular duct 112 and through a sampling medium 120, after which it encounters a 90° bend 115 in the duct before venting from the sampler via an exit outlet 130. The 90° bend 115 serves four purposes.

Firstly, the 90° bend 115 directs air to leave the sampler 110 through an outlet 130 that faces downwards and so does not admit rain or other precipitation.

Secondly, the 90° bend 115 directs the exiting air away from the horizontal centre-axis of the duct and out of the bottom of the sampler. The exiting air is thereby hindered from rising and entering the opposite channel on the leeside of the sampler 110, where it could otherwise cause an unwanted backflow that would be sampled by the sampling medium disposed in the diametrically opposite section.

Thirdly, the 90° bend 115 generates a centrifuging motion, which has the effect of changing the lateral speed profile of the flow as it rounds the bend. This centrifuging motion is shown schematically in FIG. 2: it has the effect that speeds are higher round the outside of the bend 115 and lower round the inside of the bend 115. The difference in speeds between the outside and the inside of the bend 115 depends on the speed of the airflow through the channel 112, which in turn depends on the ambient wind speed approaching the inlet horn 114. Specifically, the difference depends on the square of the air speed, so that there is a relatively greater difference in higher wind-speed situations and a relatively lesser difference in lower wind-speed situations. It follows that pollutants that are associated with higher wind-speed situations will exhibit greater differences in their flux rates between the inside and outside of the bend than pollutants that are associated with lower wind-speed situations. Therefore, the difference in flux rates between the inside and the outside of the bend can be used to discern some information regarding the ranges of inlet wind speeds that are associated with particular pollutants. Further information on how the 90° bend is used to distinguish between the wind-speeds regimes that are associated with different pollutants is given below in relation to the eighth embodiment of the invention.

Fourthly, the 90° bend 115 directs air leaving the outlet 130 so that it is inserted into the external flow of air around the underside of the sampler. This insertion causes an interaction according to the Coanda effect, that helps to prevent flow separation as the external airflow rounds the underside of the sampler. This effect helps the airflow to follow the shape of the sampler here, and to maintain its speed rather than having it reduced by turbulence in a zone of separated flow. The maintained air speed promotes a Bernoulli effect due to the flow of external air past the outlet 130, which helps to draw air into the inlet horn 114, though parallel-sided duct 112, through the sampling medium 120, and out of the outlet 130.

FIG. 1B shows that an airflow approaching the sampler along the centre-line of any channel has a direct frontal encounter with the inlet horn 114 and the sampling medium 120 in that channel. By contrast, the same airflow only encounters the horns or sampling media of the other channels obliquely (if on the windward side of the sampler) or not at all (if on the leeward side). The contrast between the direct frontal flow in the downwind channel, and the oblique or absent flows in the other channels, enables the sampler to distinguish between pollutants coming from different directions. The sampler is designed to maximise these contrasts, so that its ability to distinguish between pollutants coming from different directions and sources is also maximised.

In order to maximise the directional discrimination of the sampler 100, it is desirable to minimise the potential for unwanted backflows to enter the outlets 130 of channels lying to leeward of whatever channel is upwind in any situation. This is because such backflows may cause pollutants to be sampled on media that are not in the appropriate upwind channel, so that the ability of different samples to discriminate between pollutants coming from different directions is reduced. The sampler incorporates three features in order to minimise unwanted backflows.

Firstly, as explained above, the 90° bend 115 directs air downwards from the bottom of the sampler so that this air it is hindered from rising and entering the outlet from the leeside channel(s).

Figure 2:
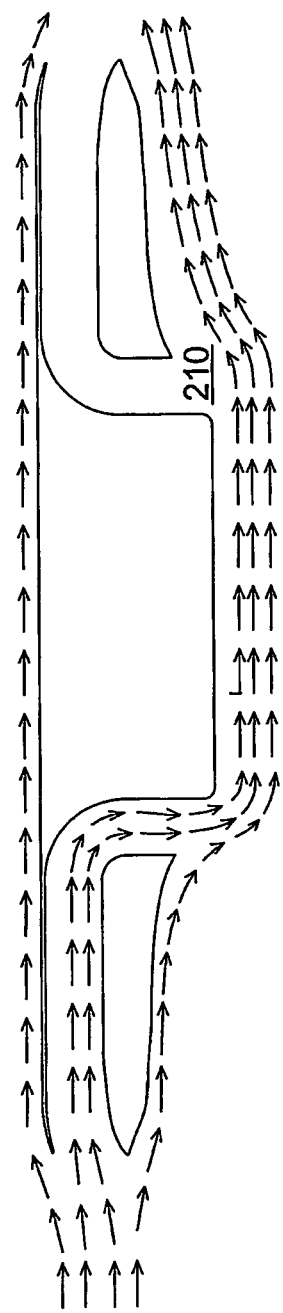
FIG. 2 shows a schematic illustration of air flowing through a central cross section of the first embodiment of the present invention.

Secondly, as shown on FIG. 2, the underside of the sampler is shaped so that there is a region of separated flow 210 formed at the outlet of the leeside channel, which hinders the external airflow from entering the leeside channel. The formation of this separated flow is assisted by the relatively abrupt curvature of the underside at this point, and by the absence of any Coanda effect from flow leaving the leeside channel (in contrast to the situation at the windward channel).

Thirdly, as shown on FIGS. 1A, 1B and 1C, the underside of the sampler is fitted with an array of deflector fins 140 that help to divert flows away from the outlets of channels that are not aligned with the wind.

FIG. 1 shows a first embodiment of the invention which contains a porous sampling medium 120 located in the parallel-sided rectangular duct 112 as a means of collecting airborne pollutants. FIGS. 3A-I show alternative embodiments that use different systems within the duct to sample a range of pollutants, including gases, particles, suspended pollutants and deposited pollutants.

Figure 3A:
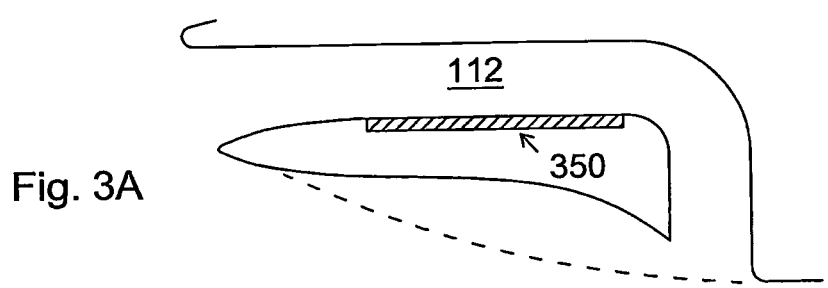
FIG. 3A shows part of a central cross sectional view through one section of a second embodiment of the present invention.

FIG. 3A shows a second embodiment that contains a flat receptor surface 350 flush with the bottom of the duct 112. The receptor may be a white paper that is darkened by deposited pollutants from the relevant wind direction, so that the amount of pollution can be assessed by using a reflectometer to measure the change in the paper's albedo over a sampling period. Alternatively, the receptor may be a microscope slide that is coated with a sticky film in order to trap and accumulate pollutants arriving in air from the relevant wind direction.

Figure 3B:
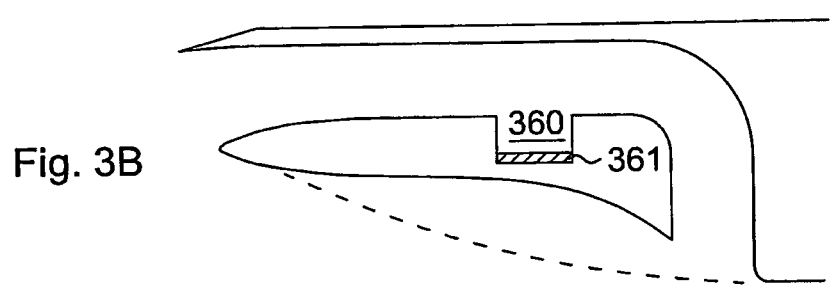
FIG. 3B shows part of a central cross sectional view through one section of a third embodiment of the present invention.

FIG. 3B shows a third embodiment that incorporates a well 360 in the bottom of the duct. The bottom of the well may be left empty as a simple trough for collecting deposited particulates. Alternatively, it may be lined with a pollutant-absorbing surface 361 (e.g. a mesh coated with a pollutant-absorbing compound) that retains and accumulates gaseous pollutants.

Figure 3C:
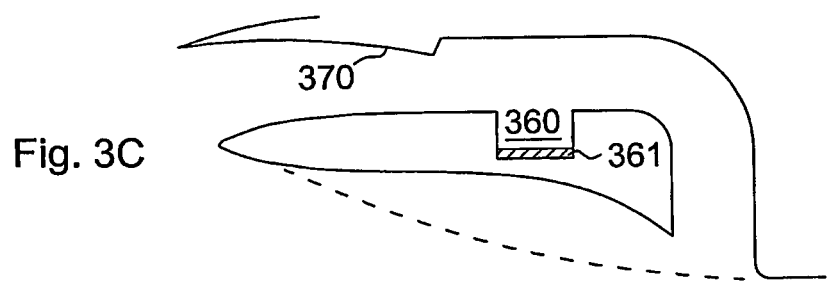
FIG. 3C shows part of a central cross sectional view through one section of a fourth embodiment of the present invention.

FIG. 3C shows a fourth embodiment that incorporates a well 360 in the bottom of the duct containing a pollutant-absorbing surface 361. It also contains a deflector ramp 370 located upwind of the well on the top of the duct. When air flows past this ramp it helps to deflect the flow into the well, which has the effect of increasing the rate at which pollutants enter the well and are collected.

Figure 3D:
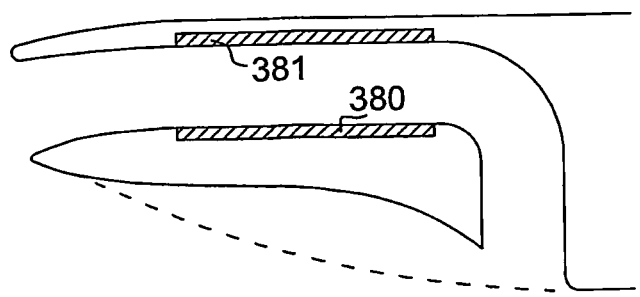
FIG. 3D shows part of a central cross sectional view through one section of a fifth embodiment of the present invention.

FIG. 3D shows a fifth embodiment in which there are pollutant-absorbing surfaces 380, 381 lying flush with all 4 walls of the parallel-side duct (the section shown in FIG. 3D shows just the upper and lower walls). These surfaces may comprise a denuder tube that progressively strips and retains pollutants from the airflow as it travels through the duct.

Figure 3E:
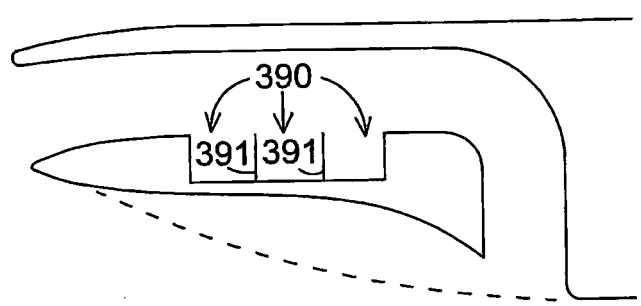
FIG. 3E shows part of a central cross sectional view through one section of a sixth embodiment of the present invention.

FIG. 3E shows a sixth embodiment in which there is a series of separate wells 390 set into the bottom of the duct. These wells are designed to trap and retain deposited particulates, and the intervening walls 391 are designed to hinder any loss of accumulated particulates by "blow out".

Figure 3F:
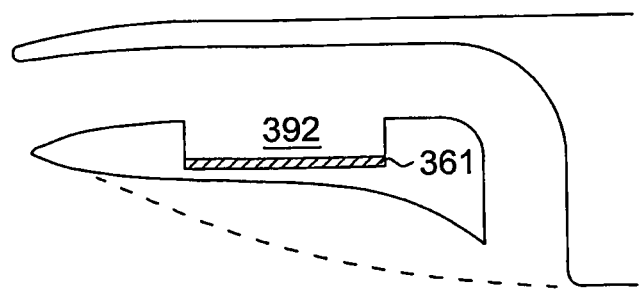
FIG. 3F shows part of a central cross sectional view through one section of a seventh embodiment of the present invention.

FIG. 3F shows a seventh embodiment in which there is a single long well 392 whose bottom is lined with a pollutant-absorbing medium 361. This long well is designed to trap and retain a larger quantity of pollutants than would be possible with the smaller well 360 shown in FIG. 3B.

Figure 3G:
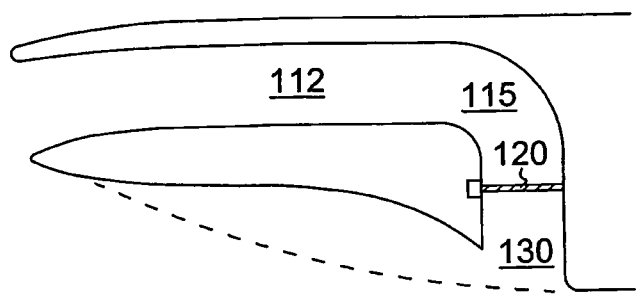
FIG. 3G shows part of a central cross sectional view through one section of an eighth embodiment of the present invention.

FIG. 3G shows an eighth embodiment in which a porous sampling medium 120 is located in the parallel-sided duct 112 between the 90° bend 115 and the outlet 130. As explained previously, the centrifuging flow around the bend 115 will cause a difference between the wind speeds on the inside and outside of the bend. There will therefore be a difference between the fluxes of pollutants passing these points. The amount of the difference in flux depends on the wind speed in the duct 112, and some of this difference will still be present in the airflow when it meets the porous sampling medium 120 located downstream of the bend. By measuring the differences between levels of pollutants sampled at different positions across the medium (i.e. towards the inside and the outside of the bend), it may be possible to discern information about the wind speeds that accompany pollution from the relevant direction. This wind speed differentiation is likely to be important for distinguishing between certain different sources of air pollutants. For example, wind-blown dusts and gaseous pollutants from elevated sources, such as chimney stacks and aircraft, are characterised by concentrations that increase with increasing wind speed. By contrast, pollutant concentrations from low-level sources such as roads decrease with increasing wind speed.

Figure 3H:
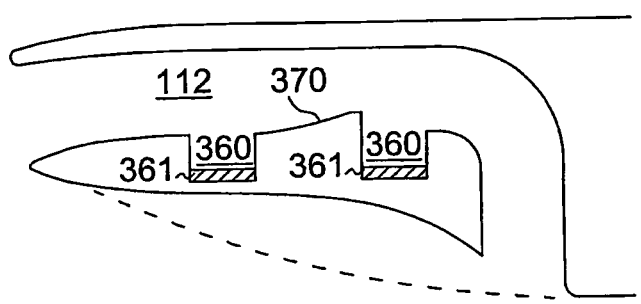
FIG. 3H shows part of a central cross sectional view through one section of a ninth embodiment of the present invention.

FIG. 3H shows a ninth embodiment in which a deflector ramp 370 is located on the bottom of the duct between two wells 360 whose bottoms are lined with pollutant-absorbing surfaces 361. This embodiment is also designed to help differentiate how much pollution arrives under different wind speeds. When wind speeds are lower, the airflow will tend to bypass the second (downwind) well because the deflector ramp will cause it to fly over this well, so that in collects less. By contrast, when wind speeds are higher there will be more tendency for the ramp to generate turbulent eddies in its wake that will allow pollutants to reach the second well. By contrast, the first well is always up wind of the ramp 370 so that it will not experience these differential effects related to wind speed. The difference in pollutants trapped in the two wells may therefore help to discern the way in which concentrations depend on wind speed in the relevant sector, and hence to discern the type of source.

Figure 3I:
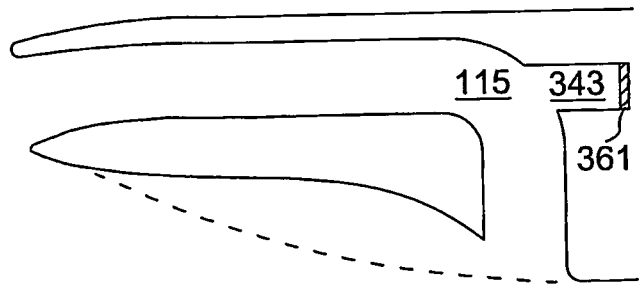
FIG. 3I shows part of a central cross sectional view through one section of a tenth embodiment of the present invention.

FIG. 3I shows a tenth embodiment in which a cavity 393 containing a pollutant-absorbing surface 361 at its closed end is located on the outside of the 90° bend 115. This cavity is positioned so that some of the centrifuging flows containing air pollutants will enter the cavity as they round the bend and be collected by the surface. The horizontal length of the cavity can be chosen to control the proportion of such centrifuging flows that penetrate to the absorbing surface. This means that the length can be chosen so that the amounts of pollution collected are within the surface's range of operation i.e. more than the minimum amount for pollutants to be detected but less than the maximum amount to avoid saturation.

The embodiments in FIGS. 3A-1 show how the original duct 112 in FIG. 1A can be used to house a range of media and cavities for passive sampling of airborne pollutants from a particular wind direction. The media and cavities include reflectometer papers, coated microscope slides, wells containing meshes with pollutant-absorbing coatings, denuder tubes, grit and dust collectors, and particulate filters. The ducts may also be used to house other passive sampling systems so that they are ventilated selectively according to the direction of the wind e.g. semi-permeable membrane devices. A further possibility is that materials coated with depurants may be placed in each channel, so that the "run-of-wind" through the channel during a period of sampling can be assessed from the loss of depurant due to airflows through the channel. In every case the flow of pollution from a selected directional arc is channelled into the relevant duct and through or over the appropriate medium or cavity, where pollution is collected over the period of sampling. At the end of this period the accumulated sample can be returned to the laboratory for measurement and/or analysis.

The sampling systems in the embodiments in FIGS. 1A-C and 3A-I can all be mounted in detachable carousels. The carousels make it quicker and easier to change samples between periods of monitoring. The carousels can also be fitted with shielding devices to protect and isolate the samples during transport to and from the laboratory prior to deployment or analysis. The sampling efficiencies of the various systems must be calibrated for different pollutants and wind speeds, so that the amounts sampled can be interpreted in terms of ambient pollutant fluxes and concentrations. This calibration can be done by connecting a pollutant gas generator to a mass flow controller, so that controlled quantities of pollutants are introduced into a wind tunnel containing a sampler that is exposed to a predetermined flow of pollutants in air. The sampling efficiency is then obtained by comparing the amount of a given pollutant collected on the sampler with the amount to which the sampler was exposed.

Embodiments of the present invention therefore offer many advantages over prior art solutions. In particular, they offer the opportunity to collect directional fluid-flow data using only a small passive device, which does not require a power source (either internal or external) or a special housing (e.g. a building in a fenced enclosure, a trailer, a large vandal-proof container), and so opens up many more potential sites for directional pollution monitoring.

The relatively low cost of a device, according to an embodiment of the invention, is likely to mean that several can be deployed at various geographical positions and vertical heights above ground around a suspected site, allowing more data to be generated and leading to a more accurate analysis of the situation. Also, the low cost of the devices makes it practical to deploy them in quantity in situations where some devices may be lost due to vandalism.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An unpowered passive sampling device for sampling fluid-borne material comprising a plurality of inlet channels, each respective inlet channel facing and receiving a fluid flow from a different associated direction and having a respective outlet channel with a pathway defined between each inlet channel and outlet channel, and a plurality of sampling mediums arranged with a sampling medium between each respective inlet channel and associated outlet channel, each medium being disposed along a substantially unobstructed fluid flow from the respective inlet channel to the respective outlet channel such that a sampling medium exposed to a single inlet channel is exposed to fluid flow from said direction associated with said single inlet channel before the fluid flows from the associated outlet channel, thereby allowing separation and collection of fluid-borne material from fluid from a plurality of different directions without moving parts, wherein each pathway includes an approximately 90° bend intermediate its respective sampling medium and outlet channel for hindering reverse flow into the respective outlet channel.

2. The sampling device of claim 1 wherein the device comprises as many inlet channels as are required for a given angular resolution.

3. The sampling device of claim 1 being configured to be self-guidable to receive fluid into whichever inlet channel is facing upwind at any given time.

4. The sampling device of claim 3 being configured to hinder fluid from entering inlet channels that are not then facing upwind.

5. The sampling device of claim 3 being configured such that fluid flows through each inlet channel occur substantially in one direction only, and that fluid flows in the opposite direction are substantially prevented.

6. The sampling device of claim 1 comprising a cavity within each inlet channel for sampling of airborne pollutants that arrive from the direction from which the fluid flow arrives.

7. The sampling device of claim 1 wherein the inlet channels are configured to provide a degree of differentiation for samples associated with relatively higher or lower wind speeds.

8. The sampling device of claim 7 wherein the degree of differentiation is provided by the bend in the pathway which causes differential changes in fluid flow through the pathway.

9. An unpowered passive sampling device for sampling fluid-borne pollutants comprising a plurality of channels each having an inlet, each respective channel defining a pathway from its respective inlet to one of a plurality of sampling mediums and a respective outlet, a sampling medium being positioned along each channel allowing unobstructed fluid flow between each inlet and its respective outlet, each inlet facing and receiving a fluid flow from a different associated direction, such that a sampling medium connected to a particular inlet by an associated channel is exposed to fluid flow and pollutants carried therein from said direction associated with the inlet to said associated channel thereby separating pollutants from the fluid and allowing identification of the direction of a flow from which pollutants collected by the medium are carried, the plurality of inlets being positioned and configured to receive fluid flow from directions cumulatively covering 360°, and each respective channel including an approximately 90° bend intermediate its respective sampling medium and outlet for hindering reverse flow into the respective outlet.

10. The sampling device of claim 9, comprising an underside, wherein each outlet is positioned to allow fluid flow out from the respective channel at the underside.

11. The sampling device of claim 10, wherein the underside defines a surface with a second bend downstream from each of the respective outlets for assisting in hindering the reverse flow.

12. The sampling device of claim 11, comprising a plurality of deflector fins extending from the underside surface, at least one deflector fin being positioned radially between each respective outlet.

13. The sampling device of claim 10, comprising a plurality of deflector fins extending from the underside surface, at least one deflector fin being positioned radially between each respective outlet.

14. The sampling device of claim 1, comprising an underside, wherein each outlet channel is positioned to allow fluid flow out from the respective pathway at the underside.

15. The sampling device of claim 14, wherein the underside defines a surface with a second bend downstream from each of the respective outlet channels for assisting the hindering of reverse flow.

16. The sampling device of claim 15, comprising a plurality of deflector fins extending from the underside surface, at least one deflector fin being positioned radially between each respective outlet channel.

17. The sampling device of claim 14, comprising a plurality of deflector fins extending from the underside surface, at least one deflector fin being positioned radially between each respective outlet channel.

18. The sampling device of claim 1, comprising an underside surface with a plurality of deflector fins, at least one deflector fin being positioned radially between each respective outlet channel.

* * * * *